United States Patent
Jungnickel et al.

(10) Patent No.: US 8,304,938 B2
(45) Date of Patent: Nov. 6, 2012

(54) OSCILLATORY SYSTEM FOR A MOTORIZED DRIVE UNIT

(75) Inventors: Uwe Jungnickel, Koenigstein/Taunus (DE); Benedikt Heil, Ober-Moerlen (DE)

(73) Assignee: Braun GmbH, Kronberg (DE)

( * ) Notice: Subject to any disclaimer, the term of this patent is extended or adjusted under 35 U.S.C. 154(b) by 271 days.

(21) Appl. No.: 12/769,704

(22) Filed: Apr. 29, 2010

(65) Prior Publication Data

US 2010/0277013 A1   Nov. 4, 2010

(30) Foreign Application Priority Data

May 2, 2009 (EP) .................................. 09006043

(51) Int. Cl.
*H02K 33/00* (2006.01)
(52) U.S. Cl. .......................... 310/36; 15/22.1
(58) Field of Classification Search ................ 310/36, 310/37, 15; 15/22.1
See application file for complete search history.

(56) References Cited

U.S. PATENT DOCUMENTS

| | | | |
|---|---|---|---|
| 5,189,751 A * | 3/1993 | Giuliani et al. ............ | 15/22.1 |
| 7,067,945 B2 * | 6/2006 | Grez et al. ............... | 310/50 |
| 2006/0255665 A1 * | 11/2006 | Kraus et al. .............. | 310/36 |
| 2008/0106156 A1 * | 5/2008 | Reishus et al. ............ | 310/36 |

FOREIGN PATENT DOCUMENTS

| | | |
|---|---|---|
| WO | WO 03/054414 | 7/2003 |
| WO | WO 03/092535 | 11/2003 |
| WO | WO 2005/062445 A1 | 7/2005 |
| WO | WO 2008/053455 | 5/2008 |

OTHER PUBLICATIONS

European Search Report for Z-8374MQ dated Oct. 9, 2009.

* cited by examiner

*Primary Examiner* — Nguyen N Hanh
(74) *Attorney, Agent, or Firm* — John P. Colbert

(57) ABSTRACT

An oscillatory system for a motorized drive unit for the generation of a rotary oscillatory movement is provided. The system includes a first oscillatory component and a second oscillatory component, the components capable of oscillating relative to one another around an axis of oscillation; and at least two elongate spring elements, each spring element having a first fastening point and a second fastening point spaced apart from one another. The spring elements are elastic in the direction of the rotary oscillatory movement. For each spring element the first fastening point is connected to the first oscillatory component and the second fastening point is connected to the second oscillatory component such that the spring elements intersect at the axis of oscillation, the axis of oscillation having an angle of intersection different from 0 degrees.

15 Claims, 8 Drawing Sheets

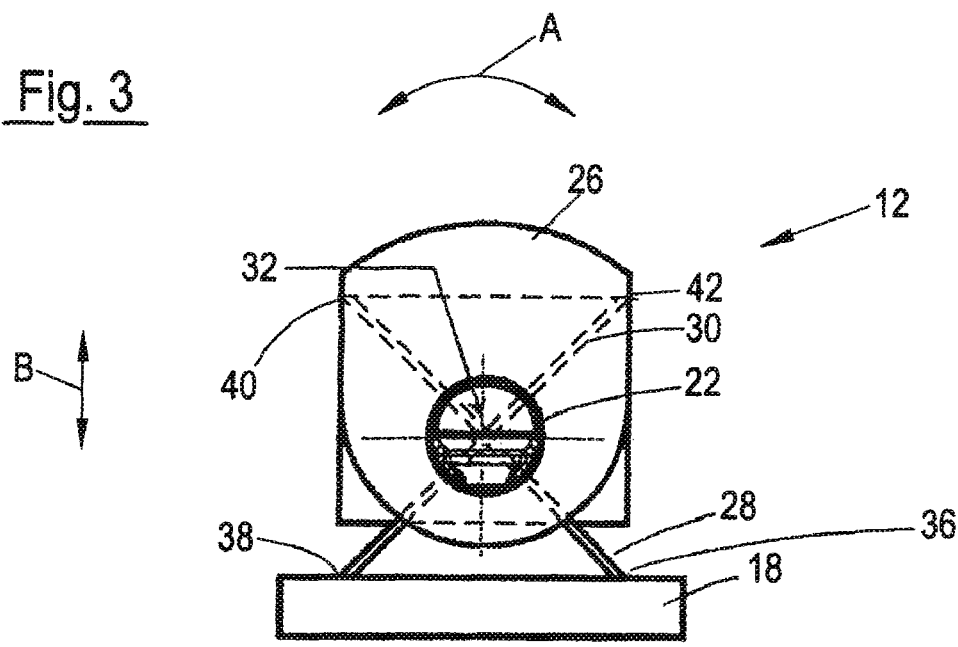
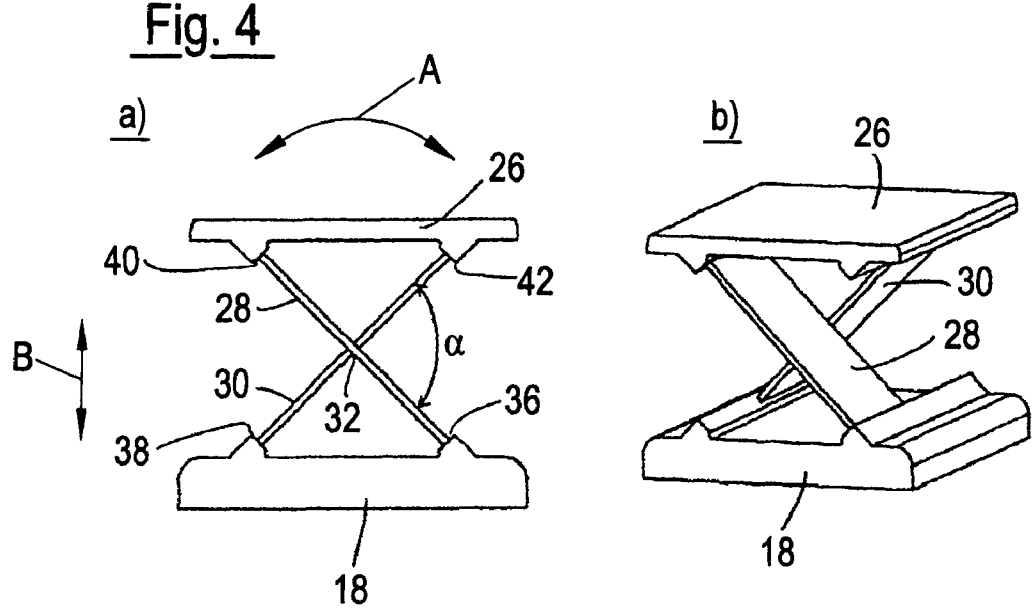

OSCILLATORY SYSTEM FOR A MOTORIZED DRIVE UNIT

CROSS REFERENCE TO RELATED APPLICATIONS

This application claims the benefit of European Patent Convention Application No. 09 006 043.5, filed on May 2, 2009, the substance of which is incorporated herein by reference.

FIELD OF THE INVENTION

The present disclosure relates generally to an oscillatory system for a motorized drive unit for the generation of a rotary oscillatory movement. The present disclosure also relates to an oscillatory system having a first component and a second component able to oscillate relative to one another around an axis of oscillation, and more particularly to a small electric appliance having an oscillatory system having a motorized drive unit that includes an electromagnetic drive element.

BACKGROUND OF THE INVENTION

Oscillatory systems are used in direct drives which can carry out movements without any further mechanical transmission elements. It is, for example, desirable in the drive of electric toothbrushes to generate a rotary oscillatory movement around a drive shaft axis and, in addition, a translatory oscillatory movement, for example, a radial movement. For this purpose, the drive represents an oscillatory system which can oscillate in a plurality of degrees of freedom. The journaling of the two components able to oscillate with respect to one another is realized in this respect by ball bearings, for example.

A drive unit which can generate a movement having a plurality of degrees of freedom, of which one in particular is a rotary oscillatory movement, is described in WO 2005/062445 A1.

It is desirable to set forth an oscillatory system for a motorized drive unit for the generation of a relative rotary oscillatory movement, said oscillatory system realizing a journaling and spring function in a simple manner and enabling a compact structure of a motorized drive unit. Accordingly, there is a need for an oscillatory system having the features described herein.

SUMMARY OF THE INVENTION

In one embodiment, an oscillatory system for a motorized drive unit for the generation of a rotary oscillatory movement includes a first oscillatory component and a second oscillatory component, the components capable of oscillating relative to one another around an axis of oscillation; and at least two elongate spring elements, each spring element having a first fastening point and a second fastening point spaced apart from one another. The spring elements are elastic in the direction of the rotary oscillatory movement. For each spring element the first fastening point is connected to the first oscillatory component and the second fastening point is connected to the second oscillatory component such that the spring elements intersect at the axis of oscillation, the axis of oscillation having an angle of intersection different from 0 degrees.

In another embodiment, a motorized drive unit for the generation of a rotary oscillatory movement includes an electromagnetic drive element having an output axle; and an oscillatory system. The oscillatory system includes a first oscillatory component and a second oscillatory component, the components capable of oscillating relative to one another around an axis of oscillation; and at least two elongate spring elements, each spring element having a first fastening point and a second fastening point spaced apart from one another. The spring elements are elastic in the direction of the rotary oscillatory movement. For each spring element the first fastening point is connected to the first oscillatory component and the second fastening point is connected to the second oscillatory component such that the spring elements intersect at the axis of oscillation, the axis of oscillation having an angle of intersection different from 0 degrees. A first oscillatory component is rotationally fixed to the electromagnetic drive element and the second oscillatory component is connected to the output axle.

BRIEF DESCRIPTION OF THE DRAWINGS

While the specification concludes with claims which particularly point out and distinctly claim the subject matter that is regarded as the invention, it is believed the various embodiments will be better understood from the following description taken in conjunction with the accompanying drawings, in which:

FIG. 3 is a plan view taken along line DI of FIG. 2;

FIG. 4a is a plan view of an oscillatory system in accordance with one embodiment;

FIG. 4b is a perspective view of the oscillatory system of FIG. 4a;

FIG. 6a is a plan view of an oscillatory system in accordance with another embodiment;

FIG. 6b is a perspective view of the oscillatory system of FIG. 6a;

FIG. 7a is a perspective view of an oscillatory system in accordance with another embodiment;

FIG. 7b is an end view taken along line VII b of FIG. 7a;

FIG. 7c is a side view of the oscillatory system taken along line VII c of FIG. 7a, showing a first operating state;

FIG. 7d is a side view of the oscillatory system taken along line VII c of FIG. 7a, showing a second operating state;

FIG. 8a is a perspective view of an oscillatory system in accordance with another embodiment;

FIG. 8b is a side view of the oscillatory system taken along line VII b of FIG. 8a;

DETAILED DESCRIPTION OF THE INVENTION

Figure 1:
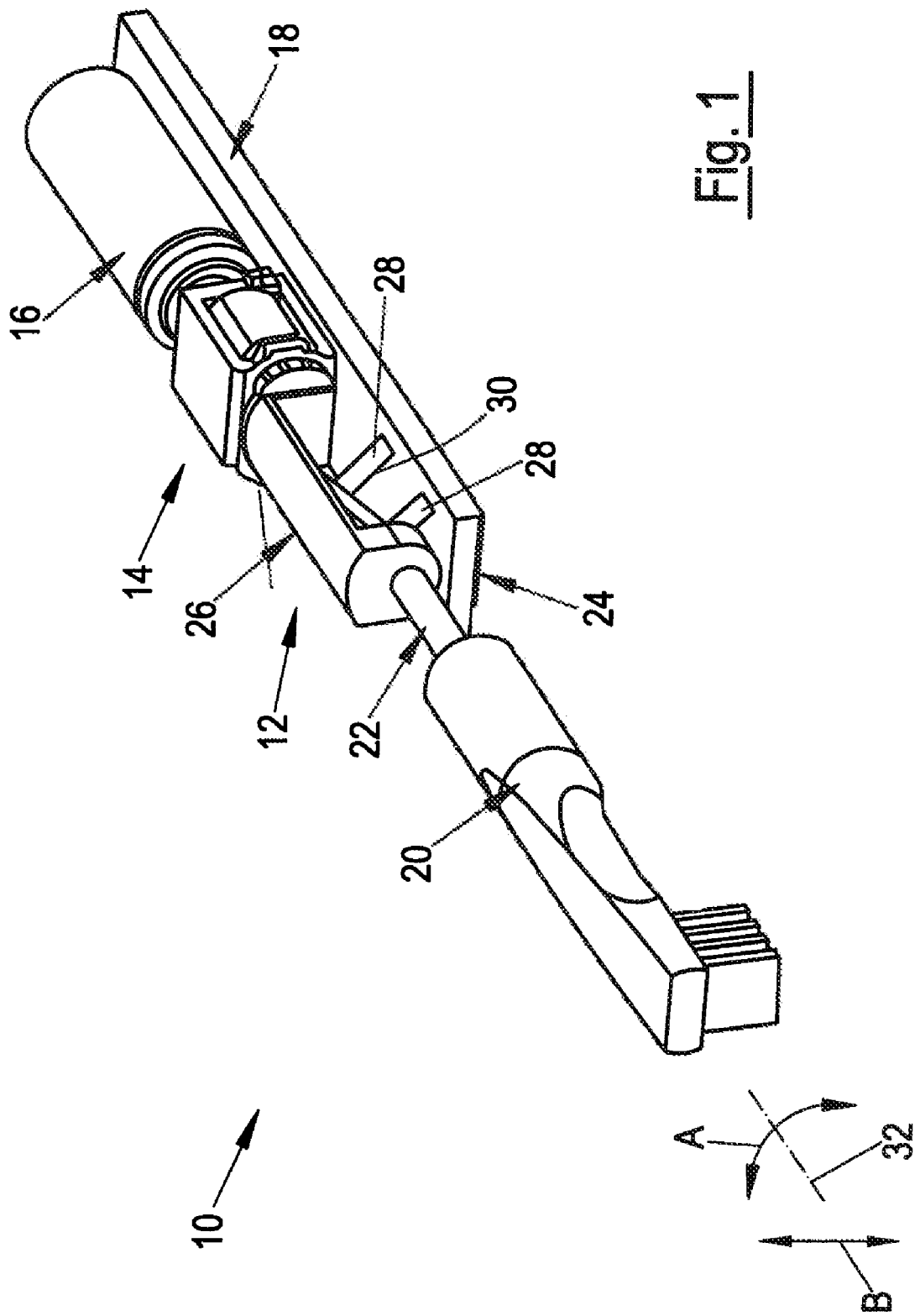
FIG. 1 is a perspective and partly open view of an electric toothbrush with an oscillatory system in accordance with one embodiment.

According to the present disclosure, an oscillatory system includes a motorized drive unit for the generation of a rotary oscillatory condition. In one embodiment, the drive unit includes a first component and a second component which can oscillate relative to one another around an axis of oscillation and which carry out a relative rotary oscillatory movement with respect to one another. As described herein, the oscillatory system may include at least two elongate spring elements which are elastic at least in the direction of the rotary oscillatory movement. Each of these spring elements has two fastening points spaced apart from one another in each case. One of these fastening points is respectively connected to the first oscillatory component and the other fastening point is connected to the second oscillatory component. The spring elements therefore connect the first oscillatory component and the second oscillatory component to one another, but permit a rotary oscillatory movement due to their elasticity in its direction.

The at least two elongate spring elements are arranged such that the connection line of the fastening points of a first spring element and the connection line of the fastening points of a second spring element cross at an angle of intersection which is different from 0°. The two oscillatory components are fixedly connected to one another in this manner. Due to the elasticity of the spring elements, however, a relative rotary oscillatory movement is possible around the point of intersection of the connection lines of the respective fastening points.

The spring arrangement formed in this manner allows both the journaling and the spring function of two oscillatory components relative to one another which can be realized with relatively simple components. Other journaling elements such as ball bearings or slide bearings may be eliminated so that the oscillatory system in accordance with the present disclosure ensures a very cost-effective structure. In one embodiment, the spring elements may intersect in the axis of oscillation. In particular the virtual axis of intersection formed by the intersected spring angle is collinear to a drive axle which is rotationally driven by a motor to generate the rotary oscillatory movement.

In one embodiment, movement of the spring elements in a translatory direction radially to the axis of oscillation is also possible. This movement may be accomplished with a setting of the respective oscillatory properties, in particular of the frequency and of the amplitude, being possible in a simple manner by a suitable selection of materials and shape of the spring elements. In another embodiment, the spring elements include leaf springs whose leaf spring surfaces are parallel to a respective plane which includes the axis of oscillation. Leaf springs are simple to manufacture and provide the elasticity around an axis which is disposed in its leaf spring surface with a simultaneously higher stiffness in other spatial directions. The leaf springs may be made of any suitable material, including, for example, sheet metal. A cost-effective embodiment provides that the leaf springs of the system are bent from a common sheet metal part so that only a punching process is required.

The first and the second oscillatory components may be made of any suitable material, including, for example, plastic. In one embodiment, the plastic components may be made as injection molded plastic parts. It is then possible in a simple manner to overmold the spring elements with these plastic parts during the manufacturing process so that the first and the second oscillatory components and the spring elements are already fixedly connected to one another in the injection process. This is particularly advantageous if the spring elements include leaf springs which are bent from a common sheet metal part. In this manner, a compact and fixed unit is created of oscillatory components and spring elements. In another embodiment, the entire oscillatory system may be manufactured from plastic parts resulting in lower manufacturing costs.

The stiffness of the oscillatory system in different spatial directions can be set differently by selection of the angle of intersection between the spring elements. If the angle of intersection amounts to 90°, for example, the stiffness for a translatory movement with otherwise equal properties of the two spring elements in a direction transverse to the axis of oscillation and from one oscillatory component to the other is the same as the stiffness in the direction perpendicular thereto, with the angle of intersection between a part of a first spring element which is connected to the first oscillatory component and a part of a second spring element which is connected to the second oscillatory component being measured. The system then substantially represents a rotary bearing.

If, in contrast, an angle of intersection is selected which is not equal to 90°, the stiffness values in different transverse directions to the axis of oscillation can be selected at different levels. If, for example, an angle of intersection is selected which is less than 90°, the system is softer in a direction from the first oscillatory component to the second oscillatory component than in a direction perpendicular thereto. Alternatively or additionally to the selection of an angle of intersection differing from 90°, a different oscillatory capability can be achieved in different directions by a suitable profiling of the spring elements.

In one embodiment, spring elements may also be elastic in a direction parallel to the axis of oscillation. In this manner, an axial oscillatory movement can also be generated. The spring elements can for this purpose be selected, for example, such that they have comparable elasticity in all directions. A realization which is simple to manufacture and is reliable provides that leaf springs which have a main leaf spring surface including the axis of oscillation are also used for such an embodiment. The ends of the leaf springs in the vicinity of the fastening points are, however, in one embodiment, bent by approximately 90° so that there is also increased elasticity in the direction of the axis of oscillation in this region. If a plurality of such leaf springs are arranged next to one another, an almost linear movement is possible parallel to the axis of oscillation in this manner so that a linear bearing is realized.

The total oscillatory system can in turn be suspended in an oscillatory manner, for, example in a housing. In this embodiment, similar intersected spring arrangements, which include leaf springs, for example, can be used as for the oscillatory system itself. On a corresponding embodiment of these springs made as suspension elements, the first oscillatory component then oscillates in phase opposition to the second oscillatory component. For example, the suspension elements can be arranged substantially parallel to the spring elements. Use of an embodiment in which an oscillatory component is fastened in the housing of an electric toothbrush, will considerably reduce the oscillations which can be felt at the hand piece.

In one embodiment, a drive unit has an electromagnetic drive element and an oscillatory system. In one example, the electromagnetic drive element is in the form of an electric motor. One of the oscillatory components of the oscillatory system is rotationally fixedly connected to the electromagnetic drive element and the other oscillatory component is connected to the drive axle of the electromagnetic drive element.

In another embodiment, an electromagnetic drive element is used which provides a rotary oscillatory movement and a translatory oscillatory movement. Such a drive unit with an electromagnetic drive element is particularly suitable for the drive of a small electric appliance since a compact and simple structure is possible. Such small electric appliances which can be driven by a drive unit may include electric razors and electric toothbrushes, for example, in which a rotary oscillatory movement is frequently combined with a translatory oscillation movement. In one embodiment, a drive unit for an electric toothbrush will have the brush head being connected to one of the oscillatory components of the oscillatory system, for example, to the oscillatory component which is connected to the drive axle of the electromagnetic drive element.

An electric toothbrush 10, with the housing forming the handle being open is shown in FIG. 1. An electromagnetic drive element 14 is connected to a battery 16 for the power feed. The electromagnetic drive element and the battery are fastened to a chassis 18. A first oscillatory component forming an oscillator 26 is connected to the output of the electromagnetic drive element. Leaf spring elements 28, 30 connect the oscillator 26 to the chassis 18 which in this respect forms the second oscillatory component. A rotary output force is provided by the electromagnetic drive element 14 which results in a relative rotary oscillatory movement in the direction A between the chassis 18 and the oscillator 26. The leaf springs 28 intersect with the leaf spring 30 in the axis of oscillation 32 around which this rotary oscillatory movement takes place.

The electromagnetic drive element 14 is made such that it can additionally stimulate a translatory oscillatory movement in the direction B which can be passed on by the oscillatory system 12 in a manner described herein. The movement of the oscillator 26 is passed on via the output axle 22 of the oscillatory system 12 to the pushed-on brush head 20 which in this respect carries out a rotary oscillatory movement in direction A and a translatory oscillatory movement in direction B. A circuit board 24 is provided beneath the chassis 28.

Figure 2:
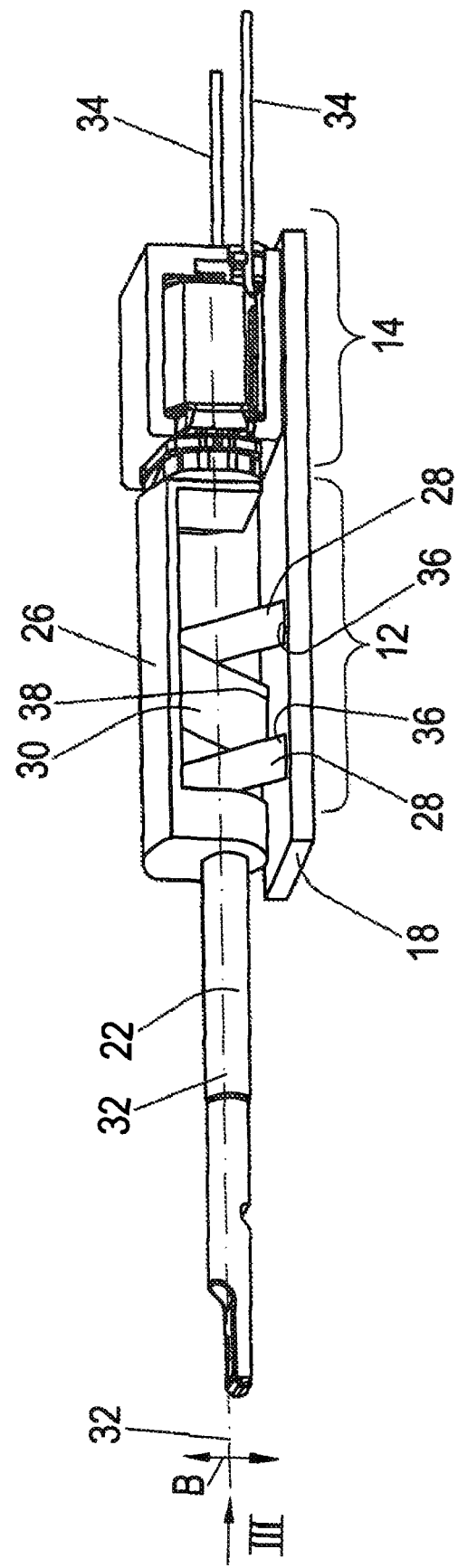
FIG. 2 is another perspective view of the electric toothbrush of FIG. 1.

As shown in FIG. 2, power feeds 34 are visible which connect the electromagnetic drive element 14 to a battery (not shown). The electric toothbrush 10 is shown without the pushed on brush head 20. The fastening points 36, 38 of the leaf springs 28, 30 at the chassis 18 are further shown in FIG. 2.

FIG. 3 depicts a partly transparently shown plan view of the embodiment of FIGS. 1 and 2 in the direction of view III, such as is set forth in FIG. 2. Here, the fastening points 40, 42 of the leaf springs 28, 30 at the oscillator 26 are additionally shown.

FIG. 4 depicts a schematic representation of an oscillatory system such as it can be used in this embodiment. Whereas FIG. 4a shows a schematic plan view in the direction of the pivot axis, FIG. 4b is a corresponding perspective representation. For reasons of clarity, however, only two spring elements 28, 30 are shown here. α designates their angle of intersection. As can in particular be recognized in FIG. 4a, the leaf springs 28, 30 intersect in the pivot axis which, on the other hand, is colinear or parallel to the output axle 22 of the electromagnetic drive element.

With respect to the embodiment shown in FIGS. 1 to 4, the electromagnetic drive element 14 generates a rotary oscillatory movement of the oscillator 26. A rotary oscillation around the axis of oscillation 32 is possible due to the crosswise arrangement of the leaf springs 28, 30. The leaf spring design of the crossed springs 28, 30 additionally enables a translatory oscillatory movement in direction B, for example. This results in a very high stiffness being given due to the cross-wise arrangement of the springs. If the electromagnetic drive element 14 additionally provides such a linear oscillatory movement, the oscillator 26 moves, on the one hand, relative to the chassis 18 around the axis of oscillation 32 and, on the other hand, carries out a pulsation movement in the direction B. By a suitable choice of the material of the springs 28, 30, their stiffness and thus the oscillatory amplitude and resonant frequency of the respective oscillation can be set to the desired degree and can optionally be selectively excited.

In the embodiment of FIG. 4, an oscillatory system is shown in which the leaf springs 28, 30 intersect at an angle α amounting to 90°. The stiffness in the linear direction B and in the linear direction C is accordingly comparable. If the angle α is selected to be less than 90°, for example 60°, the stiffness is reduced in direction B with respect to the stiffness in the direction C. In this way, the resonant frequencies of the oscillations can also be set differently in different directions and can, for example, preferably trigger the desired oscillatory manner by excitation of the respective resonant frequency.

Figure 5A:
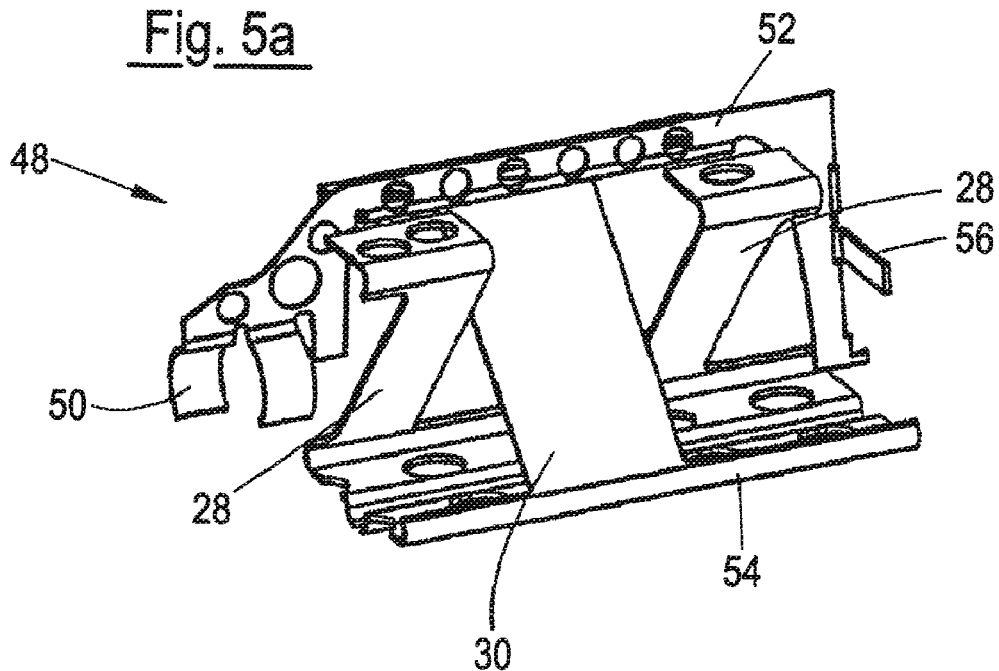
FIG. 5a is a perspective view of an oscillatory system in accordance with another embodiment.
Figure 5B:
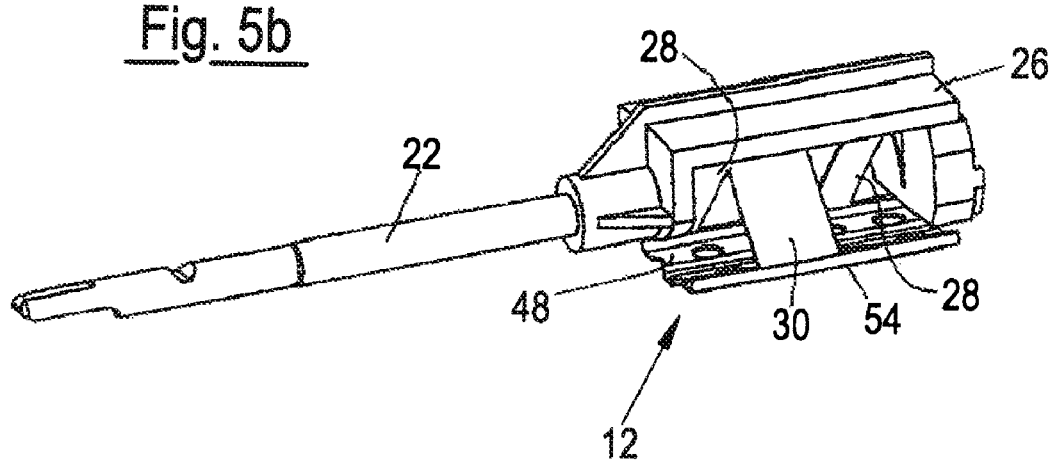
FIG. 5b is a perspective view of the oscillatory system of FIG. 5a that has been overmolded.

FIG. 5a shows a detail of the embodiment of FIGS. 1 to 4. In particular, a bent sheet metal part 48 is visible which is bent in one piece to form the leaf springs 28, 30. In this respect, the leaf springs 28, 30 are connected to one another via the chassis fastening 54 by which the bent sheet metal part 48 can be screwed, for example, to the chassis 18. A connection element 52 is, for example, fixedly connected to the part of the leaf spring 30 at the top in FIG. 5a. An enclosure for the output axle 22 of the oscillator 26 is indicated by reference numeral 50, whereas reference numeral 56 indicates a motor coupling element to the output of the electromagnetic drive element 14. The part of the bent sheet metal part 48 at the top in FIG. 5a which includes the connection element 52 and the upper parts of the spring elements 28, 30 is overmolded in the injection molding process by which the oscillator 26 is formed as a plastic part. In this manner, the bent sheet metal part 48 is fixedly connected to the oscillator 26 and/or to the chassis 18, as is shown in FIG. 5b.

Figure 6:
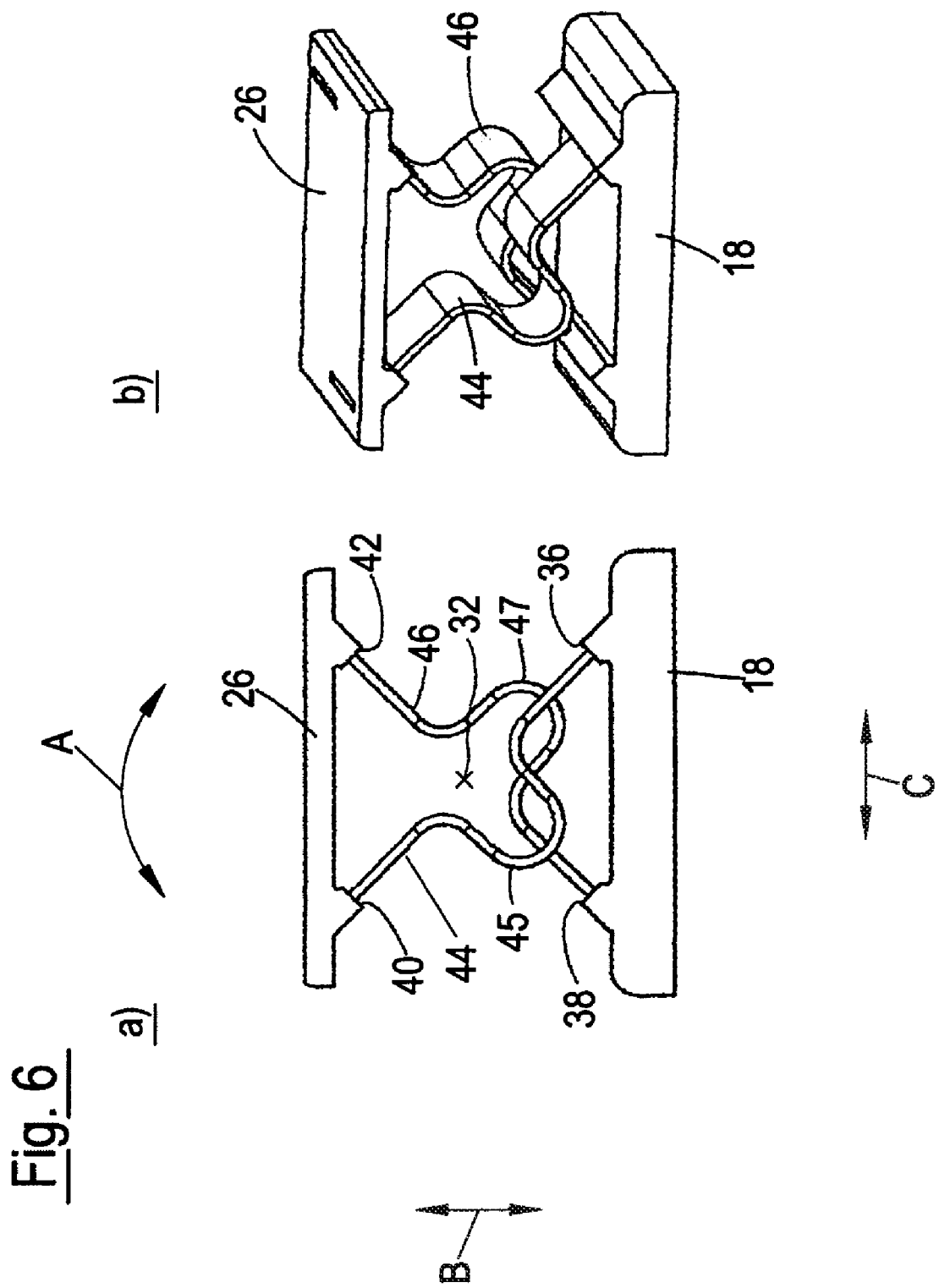

FIG. 6 depicts another embodiment of an oscillatory system. The leaf springs 44, 46 are here not made straight, but have a profiling 45, 47. The axis of oscillation 32 is furthermore located at the point of intersection of two imaginary lines between the fastening points 36, 40, on the one hand, and the fastening points 38, 42, on the other hand. However, the stiffness here is in particular reduced in the direction B due to the profiling 45, 47.

Figure 7:
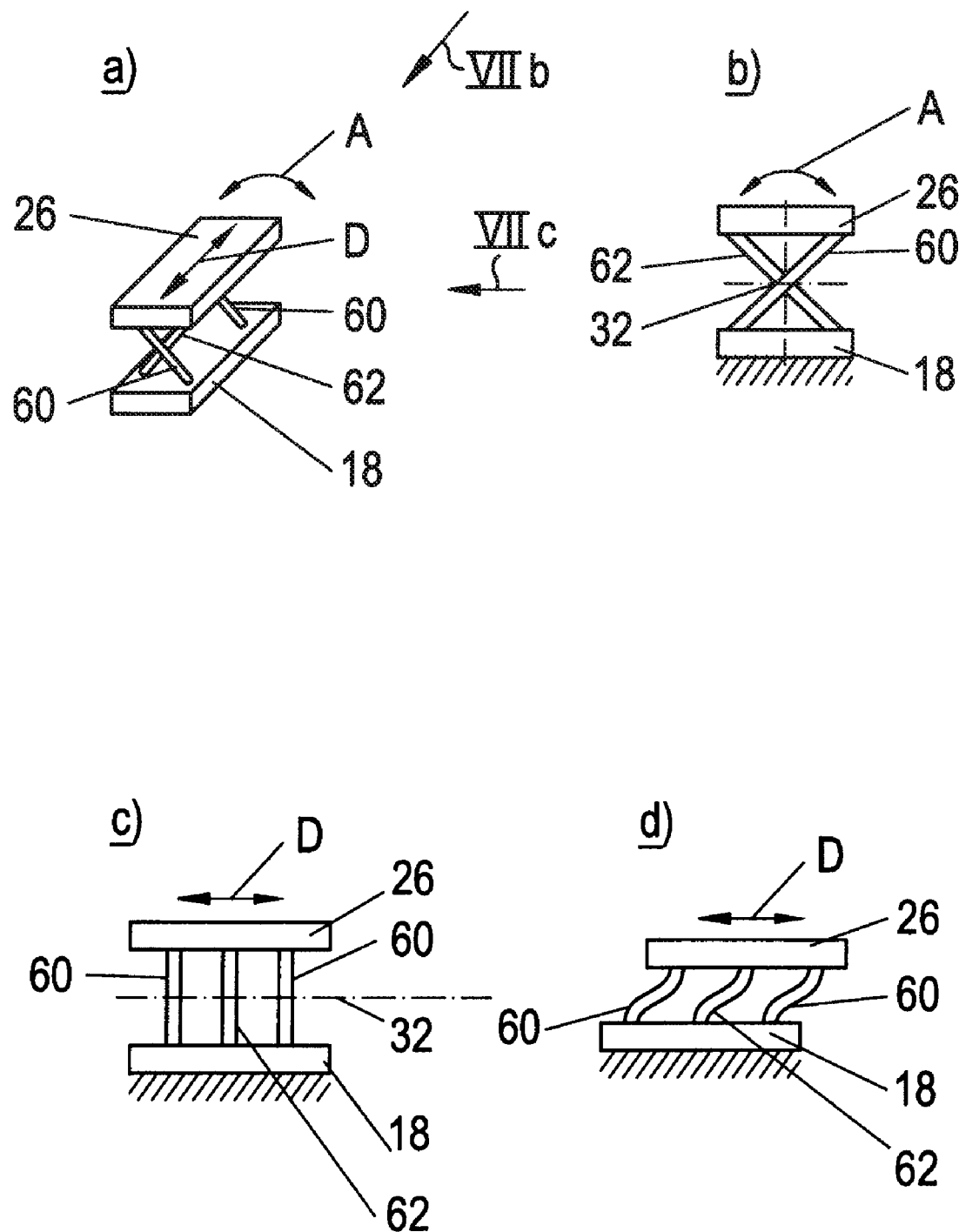

Another embodiment of an oscillatory system is shown in FIG. 7. The system as shown in FIG. 7 allows for an additional translatory oscillatory movement in direction D. In this embodiment, the spring elements 60, 62 are not made as leaf springs, but as rod springs which have an elasticity around the axis of oscillation 32 and in the axial direction D. The use of three leaf springs 60, 62 enables an almost linear movement in the direction D parallel to the axis of oscillation 32, as is indicated in FIG. 7d, which shows the same direction of view to this embodiment as FIG. 7c, only in a different operating state in which the oscillator 26 and the chassis 18 are displaced in the direction D with respect to one another. If accordingly a linear oscillatory movement along the axis of oscillation 32 is provided by the electromagnetic drive element 14 in addition to the rotary oscillatory movement in the direction A around the axis of oscillation 32 in such an embodiment, the rotary oscillatory movement A can be combined with a linear oscillation in the axial direction D.

Figure 8:
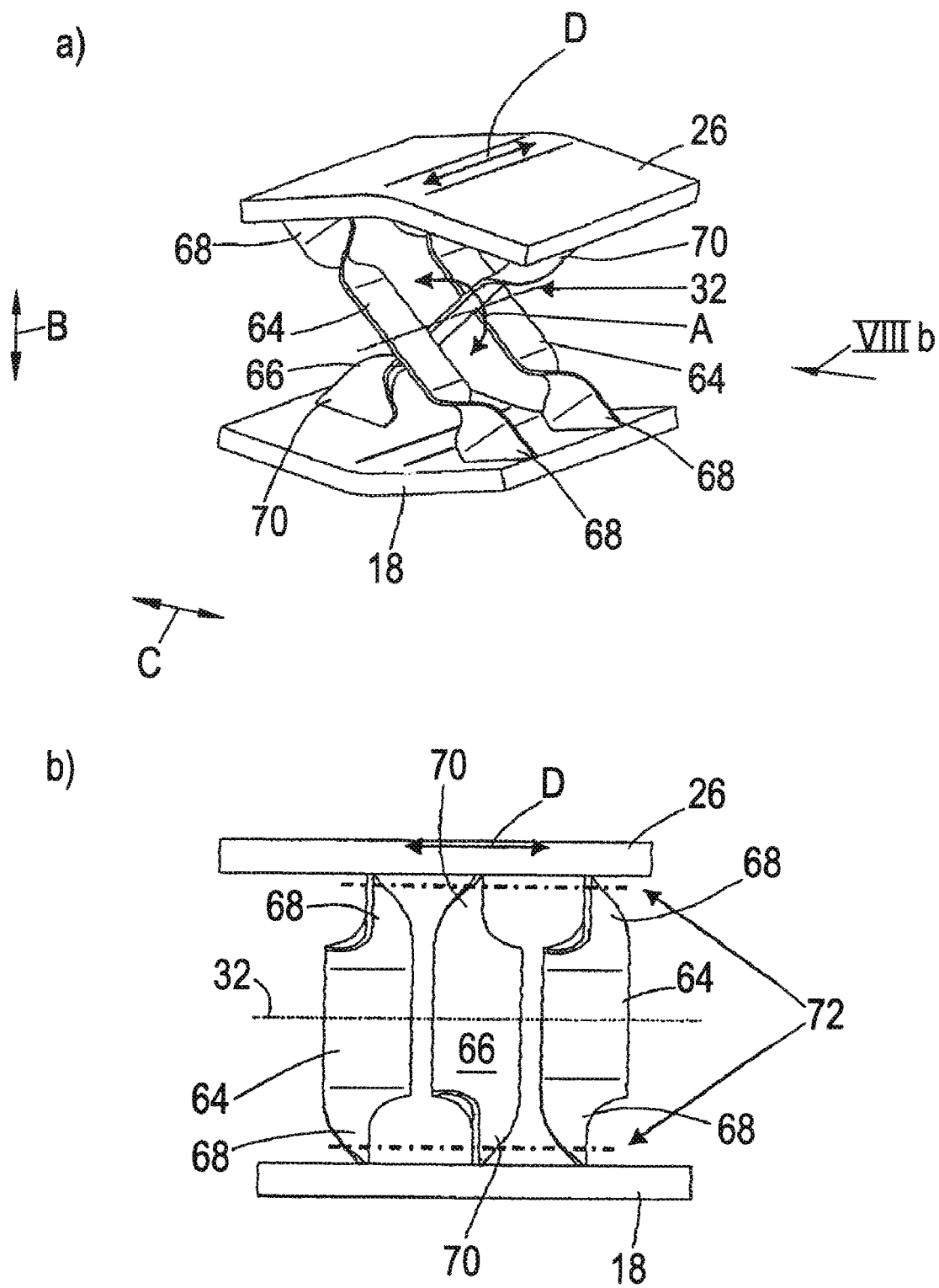

FIG. 8 shows another embodiment of the system of FIG. 7. The spring elements are made as leaf springs 64, 66, with the main leaf spring surface including the axis of oscillation 32. The ends 68, 70 of the leaf springs 64, 66 are, however, bent by 90° in the region of the fastening points to the chassis 18 or to the oscillator 26. In the region of the ends 68, 70 of the leaf springs, a respective bending plane 72 is defined in this manner which are shown in dotted line form in FIG. 8b. A reduced stiffness in the direction D is given in the region of the ends 68, 70 of the leaf springs so that the linear movement becomes possible in this direction, as is shown in FIG. 8b. The individual embodiments can naturally also be combined so that, for example, by a suitable choice of the angle of intersection between the leaf springs 64, 66 in the embodiment of FIG. 8, the stiffness in the direction B is reduced with respect to the stiffness in the direction C so that a translatory oscillatory movement in the direction B can be combined with an axial oscillatory movement in the direction D and a rotary oscillatory movement in the direction A when the electromagnetic drive element 14 stimulates corresponding movements.

Figure 9:
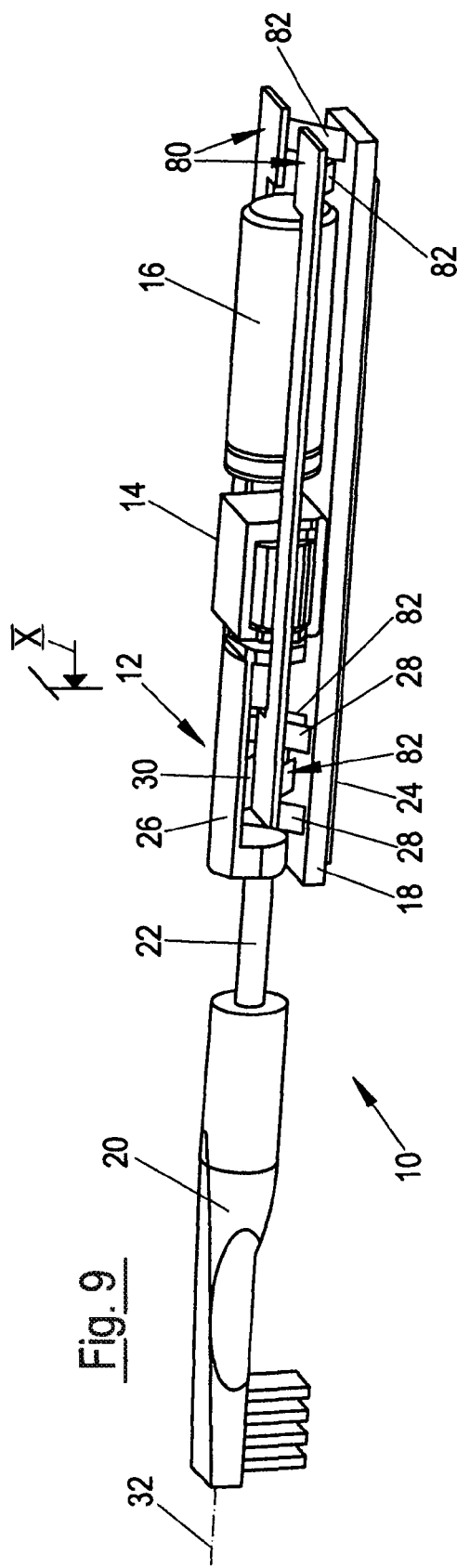
FIG. 9 is a perspective and partly open view of an electric toothbrush with an oscillatory system in accordance with another embodiment.
Figure 10:
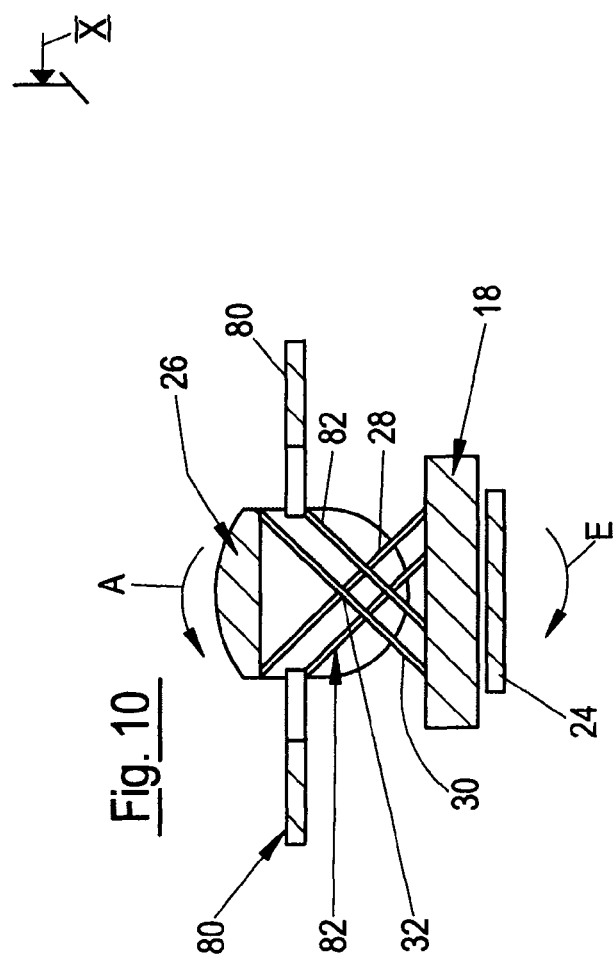
FIG. 10 is a cross-sectional view taken along line X-X of FIG. 9. The figures herein are not necessarily drawn to scale.

FIGS. 9 and 10 show embodiments of an oscillatory system 12 further comprising suspension elements 82. An electromagnetic drive element 14 is connected to a battery 16 for the power feed. The chassis 18 is connected via suspension elements 82 to frame elements 80 which are connected to the housing of the electric toothbrush not shown in FIG. 9. The suspension elements 82 are in this respect made in the same way as the spring elements 28, 30 via which the chassis 18 and the oscillator 26 are connected to one another in the described manner. The suspension elements in this embodiment include leaf springs 82 which are arranged parallel to the spring elements 28, 30. If the electromagnetic drive element 14 provides a rotary oscillatory movement, the chassis 18 oscillates in phase opposition to the oscillator 26 in the direction E. In this manner, in particular with an electric toothbrush, the vibrations onto the housing forming a handle of the electric toothbrush can be reduced.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oscillatory system for a motorized drive unit for the generation of a rotary oscillatory movement, the system comprising:
    a first oscillatory component and a second oscillatory component, the components capable of oscillating relative to one another around an axis of oscillation; and
    at least two elongate spring elements, each spring element having a first fastening point and a second fastening point spaced apart from one another, wherein the spring elements are leaf springs having surfaces that are elastic in a direction parallel to the axis of oscillation; and further wherein for each spring element the first fastening point is connected to the first oscillatory component and the second fastening point is connected to the second oscillatory component such that the spring elements intersect at the axis of oscillation, the axis of oscillation having an angle of intersection different from 0 degrees.

2. The oscillatory system according to claim 1, wherein the leaf springs are made of sheet metal.

3. The oscillatory system according to claim 2, wherein the leaf springs are formed from a common sheet metal part.

4. The oscillatory system according to claim 1, wherein the first oscillatory component and a second oscillatory component are made of plastic.

5. The oscillatory system according to claim 4, wherein the first oscillatory component and a second oscillatory component are formed as injection molded parts.

6. The oscillatory system according to claim 5, wherein the at least two spring elements are partly overmolded with the first and second oscillatory components such that the spring elements and the oscillatory components are fixedly connected to one another.

7. The oscillatory system according to claim 1, wherein the angle of intersection is 90 degrees.

8. The oscillatory system according to claim 1, wherein the angle of intersection is not equal to 90 degrees.

9. The oscillatory system according to claim 1, wherein the at least two spring elements are profiled.

10. The oscillatory system according to claim 1, wherein the surfaces of the leaf springs are parallel to a respective plane which includes the axis of oscillation and further wherein the leaf springs include ends that are angled such that the ends are perpendicular to the axis of oscillation.

11. A motorized drive unit for the generation of a rotary oscillatory movement comprising:
    an electromagnetic drive element having an output axle; and
    an oscillatory system, the oscillatory system including a first oscillatory component and a second oscillatory component, the components capable of oscillating relative to one another around an axis of oscillation; and at least two elongate spring elements, each spring element having a first fastening point and a second fastening point spaced apart from one another, wherein the spring elements are leaf springs having surfaces that are elastic in a direction parallel to the axis of oscillation; wherein for each spring element the first fastening point is connected to the first oscillatory component and the second fastening point is connected to the second oscillatory component such that the spring elements intersect at the axis of oscillation, the axis of oscillation having an angle of intersection different from 0 degrees;
    wherein a first oscillatory component is rotationally fixed to the electromagnetic drive element and the second oscillatory component is connected to the output axle.

12. The motorized drive unit according to claim 11, wherein the electromagnetic drive element is an electric motor.

13. A small electric appliance having a motorized drive unit according to claim 11.

14. A small electric appliance according to claim 13, wherein the appliance is an electric toothbrush.

15. An oscillatory system for a motorized drive unit for the generation of a rotary oscillatory movement, the system comprising:
    a first oscillatory component and a second oscillatory component, the components capable of oscillating relative to one another around an axis of oscillation;
    at least two elongate spring elements, each spring element having a first fastening point and a second fastening point spaced apart from one another, wherein the spring elements are elastic in the direction of the rotary oscillatory movement and further wherein for each spring element the first fastening point is connected to the first oscillatory component and the second fastening point is connected to the second oscillatory component such that the spring elements intersect at the axis of oscillation, the axis of oscillation having an angle of intersection different from 0 degrees; and at least two suspension elements for connecting the second oscillatory component to a housing frame.

* * * * *